United States Patent [19]

Krüger et al.

[11] 4,156,017
[45] May 22, 1979

[54] PESTICIDES

[75] Inventors: Hans-Rudolf Krüger; Clemens Kötter; Hartmut Joppien, all of Berlin, Fed. Rep. of Germany

[73] Assignee: Schering Aktiengesellschaft, Berlin and Bergkamen, Fed. Rep. of Germany

[21] Appl. No.: 770,991

[22] Filed: Feb. 22, 1977

[51] Int. Cl.$^2$ ............................ A01N 9/20; A01N 9/24
[52] U.S. Cl. .................................. 424/330; 260/570.9; 424/316
[58] Field of Search ..................... 260/570.9; 424/316, 424/330

[56] References Cited

U.S. PATENT DOCUMENTS

| | | | |
|---|---|---|---|
| 2,192,927 | 3/1940 | Morrill | 260/570.9 X |
| 2,268,129 | 12/1941 | Reppe et al. | 260/570.9 X |

OTHER PUBLICATIONS

Abbott Labs (I), "Chemical Abstracts", vol. 59, p. 3831d (1963).
Abbott Labs (II), "Chemical Abstracts", vol. 60, p. 9201b (1964).
Sweet et al., "Chemical Abstracts", vol. 63, p. 4821e (1965).

*Primary Examiner*—Robert V. Hines
*Attorney, Agent, or Firm*—Michael J. Striker

[57] ABSTRACT

The specification discloses the use of compounds having the formula:

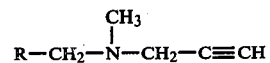

wherein R is a possibly substituted aromatic hydrocarbon radical as insecticides and ovicides.

8 Claims, No Drawings

PESTICIDES

This invention relates to pesticides, more specifically the invention relates to pesticides containing 2-propylamine derivatives, but in particular to those having insecticidal and ovicidal action.

Compounds have generally become known as inhibitors of monoamino-oxidase, to which belong, for example, trans-2-phenylcyclopropylamine sulfate, 1-isonicotinyl-2-isopropylhydrazine phosphate, isonicotinic acid-2-[-(benzylcarbamoyl)-ethyl] hydrazide, and also a 2-propinylamine derivative, such as N-benzyl-N-methyl-2-propinylamine.

It has now been found that 2-propinylamine derivatives of the general formula $$R-CH_2-\underset{\underset{CH_3}{|}}{N}-CH_2-C\equiv CH$$

in which R represents a possibly substituted aromatic hydrocarbon radical, or their salts, surprisingly develop an excellent action against harmful insects as well as against their eggs.

This action is particularly surprising and was not foreseeable since the other oxidase inhibitors named above do not show such as action.

The action found is exerted in particular against *lepidoptera*, as for instance *Spodoptera littoratis* (Egyptian cotton moth), *Mamestra brassicae* (cabbage moth) and *Pieris brassicae* (cabbage Butterfly).

The compounds to be used according to the invention are distinguished moreover by a low toxicity for warm-blooded animals. Thus, for example, for N-benzyl-N-methyl-2-propinylamine the actue LD$_{50}$ mouse p.o. is 700 mg/kg, for N-(2-chlorobenzyl)-N-methyl-2-propinylamine, 305 mg/kg.

As these compounds are, moreover, especially well tolerated by plants, they can be used to advantage against pests in plant cultivations without danger. Examples of such cultivations are cotton, tomatoes, cauliflower, bush beans, string beans, sugar beets, corn and rice.

The most favorable concentration of application for the characterized compounds is about 0.01% to 1.0%, preferably 0.05% to 0.2%.

Of the characterized compounds there can be used according to the invention in particular those in which R represents the radical

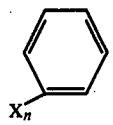

wherein X is the same or different and symbolizes hydrogen, an alkyl or alkoxy radical, a halogen atom or a nitro group, and n is an integer from 1 to 3.

Optimum effects are found, however, with those compounds wherein according to the general formula X symbolizes hydrogen, C$_1$-C$_3$ alkyl, C$_1$-C$_3$ alkoxy, chlorine or nitro.

The compounds to be used according to the invention can be employed either in the free form or in the form of their salts with inorganic or organic acids.

Of the salts, particularly the hydrochlorides are suitable for use according to the invention.

Compounds or their salts which can be preferably used according to the invention are, for example, the following without restriction thereto.

| | COMPOUND | PHYSICAL CONSTANT |
|---|---|---|
| 1. | N-(4-chlorobenzyl)-N-methyl-2-propinylamine | B.p. 96°–106° C./2 Torr |
| 2. | 4-Chlorobenzyl-methyl-2-propinyl ammonium chloride | M.p. 216.5°–217° C. |
| 3. | N-Benzyl-N-methyl-2-propinylamine | B.p. 115°–120° C./25 Torr |
| 4. | N-(2-chlorobenzyl)-N-methyl-2-propinylamine | B.p. 92°–94° C./2.5 Torr |
| 5. | N-(3-chlorobenzyl)-N-methyl-2-propinylamine | B.p. 94°–103° C./3 Torr |
| 6. | N-(3,4-dichlorobenzyl)-N-methyl-2-propinylamine | n$_D^{20}$ = 1.5497 |
| 7. | N-(2,4-dichlorobenzyl)-N-methyl-2-propinylamine | n$_D^{20}$ = 1.5485 |
| 8. | N-(3-methoxybenzyl)-N-methyl-2-propinylamine | B.p. 102°–105° C./1 Torr |
| 9. | Benzyl-methyl-2-propinyl-ammonium-chloride | M.p. 154°–155° C. |
| 10. | 2-Chlorobenzyl-methyl-2-propinyl-ammonium chloride | M.p. 160°–160.5° C. |
| 11. | 3-Chlorobenzyl-methyl-2-propinyl-ammonium chloride | M.p. 182°–183.5° C. |
| 12. | 2,4-Dichlorobenzyl-methyl-2-propinyl-ammonium chloride | M.p. 171°–172° C. |
| 13. | 3-Methoxybenzyl-methyl-2-propinyl-ammonium chloride | M.p 165°–166° C. |
| 14. | 3,4-Dichlorobenzyl-methyl-2-propinyl-ammonium chloride | M.p. 185°–186° C. |

The free bases are colorless liquids which are well soluble in organic solvents, such as hydrocarbons, halogenated hydrocarbons, ethers, ketones, alcohols, esters, carboxylic acid amides, and carboxylic acid nitriles. Their solubility in water is low. The 2-propinylamine derivatives can easily be isolated as crystalline substances in the form of their halohydrogen salts; the latter are well water-soluble, but little soluble in organic solvents.

The compounds according to the invention are well known per se or can be produced by methods known in the art.

Their production is effected, for example, by reacting propargyl halides of the general formula HC≡C—CH$_2$—Hal with N-substituted methylamines of the general formula

R—CH$_2$—NH—CH$_3$ with the use of a solvent in the presence of an acid binder, and treating the reaction products with acids, if the salts are desired, R having the above meaning and Hal being an halogen atom, preferably chlorine or bromine.

For the synthesis of the compounds to be used according to the invention, the reaction partners are used in approximately equimolecular quantities. Suitable reaction media are solvents inert to the reactants. The following may be named: Halogenated hydrocarbons, such as methylene chloride, chloroform, carbon tetrachloride, aliphatic and aromatic hydrocarbons, such as petroleum ether, cyclohexane, benzene, toluene and xylene, alcohols, such as methanol and ethanol, and ketones, such as acetone, methyl-isobutyl ketone and isophorone.

The reaction takes place between 0° and 100° C., but generally between room temperature and the reflux temperature of the respective mixture.

For binding the resulting hydrohalic acids one uses tertiary amines, for example triethylamine or N,N-dimethyl aniline, pyridine bases, or suitable inorganic bases, such as oxides, hydroxides and carbonates of the alkali and alkaline earth metals.

As a rule, the propargyl halide is added to the respective N-substituted methylamine and to the halohydrogen acceptor in portions, but the addition of the reactants may alternatively be in the reverse sequence.

After the completed reaction, the halohydrogen salt is removed by filtering, washing with the respective solvent. After removal of the solvent, the residue is fractionally distilled under reduced pressure, and one obtains the reaction products as colorless liquids.

The salt of the 2-propinylamine derivatives can, if desired, be obtained by treatment of the amines, for instance, with ether solutions of the acids while cooling.

They can easily be recrystallized from a suitable organic solvent, as for example a mixture of ethanol and ether.

The following examples will explain the production of the compounds to be used according to the invention without any limitation thereto.

(a) N-(4-Chlorobenzyl)-N-methyl-2-propinylamine

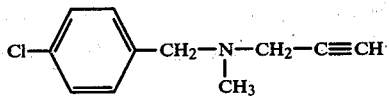

To a solution of 31.1 g (0.2 mole) N-(4-chlorobenzyl)-methylamine and 30.3 g (0.3 mole) triethylamine in 150 ml dry benzene are added in portions at room temperature while stirring 23.8 g (0.2 mole) propargyl bromide. The solution is heated for 17 hours with reflux. After filtering off the solid phase, the the solvent is distilled under vacuum and the remaining residue fractionally distilled under reduced pressure. One thus obtains 30.9 g N-(4-chlorobenzyl)-N-methyl-2-propinylamine (79% of the theory as colorless liquid of the boiling point 86°-106° C./2 Torr.

(b) 4-Chlorobenzyl-methyl-2-propinyl ammonium chloride

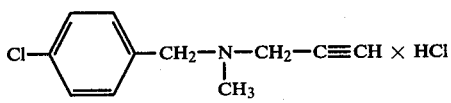

To a solution of 5 g (0.0258 mole) N-(3-chlorobenzyl)-N-methyl-2-propinylamine in 50 ml ether there are added, at 5° C., 35 ml of an HCl-saturated ether solution. The product is left standing at room temperature overnight, then the thick, white crystal paste is sucked off, washed with ether, and recrystallized out of an ethanol-ether mixture. One obtains 5.6 g (94.5% of the theory) 4-chlorobenzyl-methyl-3-propinyl ammonium chloride of the melting point 216.5°-217° C.

The other characterized compounds can be produced analogously.

The compounds to be used according to the invention can be used either alone, in mixture with one another or with other active substances. Possibly other plant protectants or pesticides may be added according to the desired purpose.

An improvement of the effect and of the rate of action can be attained, for example, by the addition of one or more action-increasing compounds, such as organic solvents, wetting agents and oils. This permits reducing the quantity of actual active substance used.

Expediently the characterized active substances or their mixtures are used in the form of preparations, such as powders, scatters, granulations, solutions, emulsions or suspensions, with addition of liquid and/or solid vehicles or diluents and possibly of wetting agents, adhesives, emulsifiers and/or dispersion aids.

Suitable liquid vehicles are, for instance, water, aliphatic and aromatic hydrocarbons such as benzene, toluene, xylene, cyclohexanone, isophorone, dimethyl sulfoxide, dimethyl formamide, also mineral oil fractions.

Suitable as solid vehicles are mineral earths, e.g. siliceous clay, silica gel, talc, kaolin, attaclay, limestone, silicon dioxide and plant products, e.g. flours.

Among surface-active substances may be named: e.g. calcium lignin sulfonate, polyoxethylene-alkylphenyl ether, naphthalene sulfonic acids and their salts, phenol sulfonic acids and their salts, formaldehyde condensates, fatty alcohol sulfates as well as substituted benzenesulfonic acids and their salts.

The proportion of the active substance or substances in the various preparations may vary within wide limits. The agents contain, for example, about 10 to 80 percent by weight of active substances, about 90 to 20 percent by weight of liquid or solid vehicles, and possibly up to 20 percent by weight of surface-active substances.

The application of the agents can be effected in the usual manner, e.g. with water as vehicle, in spray solution quantities of about 100 to 1000 liters per hectare. Use of the agent by the so-called "Low Volume" and "Ultra Low Volume" process is also possible, as is their application in the form of so-called microgranulates.

The production of these preparations can be carried out in a manner known in itself, e.g. by mixing or grinding. If desired, the individual components may be mixed just before their use, as is done in the practice, for example, in the so-called tank mixing method.

The following examples will more clearly explain the invention without limitation thereof.

EXAMPLE 1

The compounds to be used according to the invention were aqueous solutions of the salts or aqueous emulsions of the baes formulated as emulsion concentrates at the desired concentration. The same procedure was followed with the comparison agents trans-2-phenylcyclopropyl aminosulfate and 1-isonicotinyl-2-isopropyl hydrazine phosphate; in the case of isonicotinic acid-2-[2-(benzylcarbamoyl)-ethyl]hydrazide, the compound was dissolved in acetone and diluted with water to the desired concentration.

Into these active substance preparations, Egyptian cotton moth eggs, two to three days old, which had been deposited by fertilized female moths on filter paper, were immersed to complete wetting and kept in closed Petri dishes until their evaluation four days after the treatment.

The criterion for evaluation of the action was the percentual prevention of batching in comparison with untreated eggs.

The results obtained are summarized in the following table.

|   | COMPOUND | SUBSTANCE CONCENTRATION (5) | PREVENTION OF BATCHING IN % |
|---|---|---|---|
| 1. | N-(4-Chlorobenzyl)-N-methyl-2-propinylamine | 0.02 | 100 |
| 2. | 4-Chlorobenzyl-methyl-2-propinyl ammonium chloride | 0.1 | 100 |
| 3. | N-Benzyl-N-methyl-2-propinylamine | 0.04 | 100 |
| 4. | N-(2-Chlorobenzyl)-N-methyl-2-propinylamine | 0.1 | 100 |
| 5. | N-(3-Chlorobenzyl)-N-methyl-2-propinylamine | 0.1 | 100 |
| 6. | N-(3,4-Dichlorobenzyl)-N-methyl-2-propinylamine | 0.04 | 100 |
| 7. | N-(2,4-Dichlorobenzyl)-N-methyl-2-propinylamine | 0.04 | 100 |
| 8. | N-(3-Methoxybenzyl)-N-methyl-2-propinylamine | 0.1 | 100 |
| 9. | Benzyl-methyl-2-propinyl ammonium chloride | 0.1 | 100 |
| 10. | 2-Chlorobenzyl-methyl-2-propinyl ammonium chloride | 0.04 | 80 |
| 11. | 3-Chlorobenzyl-methyl-2-propinyl ammonium chloride | 0.1 | 100 |
| 12. | 2,4-Dichlorobenzyl-methyl-2-propinyl ammonium chloride | 0.1 | 100 |
| 13. | 3-Methoxybenzyl-methyl-2-propinyl ammonium chloride | 0.04 | 70 |
| 14. | 3,4-Dichlorobenzyl-methyl-2-propinyl ammonium chloride | 0.04 | 100 |
|   | COMPARISON AGENTS |   |   |
| 15. | trans-2-Phenylcyclopropyl aminosulfate | 1.0 | 0 |
| 16. | 1-Isonicotinyl-2-isopropyl hydrazine phosphate | 1.0 | 0 |
| 17. | Isonicotinic acid-2-[2-(benzylcarbamoyl)-ethyl]-hydrazide | 1.0 | 0 |

EXAMPLE 2

The compounds to be used according to the invention were used as aqueous solutions of the salts or as aqueous emulsions of the bases formulated as emulsion concentrates at the desired concentration. The same procedure was followed with the comparison agents trans-2-phenylcyclopropyl aminosulfate and 1-isonicotinyl-2-isopropyl hydrazine phosphate; in the case of isonicotinic acid-2-[2-(benzylcarbamoyl)-ethyl]-hydrazide, the compound was dissolved in acetone and diluted to the desired concentration with water.

Into these active substance preparations, cabbage moth eggs, two days old, which had been deposited by fertilized female moths on cauliflower leaves, were immersed to complete wetting and kept in closed Petri dishes until evaluation four days after the treatment.

The criterion for the evaluation of action was the percentual prevention of hatching in comparison with untreated eggs.

|   | NAME OF COMPOUND | SUBSTANCE CONCENTRATION (%) | PREVENTION OF HATCHING IN % |
|---|---|---|---|
| 1. | N-(4-Chlorobenzyl)-N-methyl-2-propinylamine | 0.06 | 100 |
| 2. | N-Benzyl-N-methyl-2-propinylamine | 0.1 | 100 |
| 3. | N-(2,4-Dichlorobenzyl)-N-methyl-2-propinylamine | 0.1 | 100 |
| 4. | 2-Chlorobenzyl-methyl-2-propinyl ammonium chloride | 0.1 | 100 |
| 5. | 3,4-Dichlorobenzyl-methyl-2-propinyl ammonium chloride | 0.08 | 100 |
|   | Comparison Agents |   |   |
| 6. | trans-2-Phenylcyclopropyl aminosulfate | 1.0 | 0 |
| 7. | 1-Isonicotinyl-2-isopropyl hydrazinephosphate | 1.0 | 0 |
| 8. | Isonicotinic acid-2-[2-(benzylcarbamoyl)-ethyl]-hydrazide | 1.0 | 0 |

EXAMPLE 3

The compounds to be used according to the invention were used as aqueous solutions of the salts or as aqueous emulsions of the bases formulated as emulsion concentrates at the desired concentration. The same procedure was followed for the comparison agents trans-2-phenylcyclopropyl aminosulfate and 1-isonicotinyl-2-isopropyl hydrazine phosphate.

With these substance preparations potted mustard seedlings on which females of the cabbage moth (Plutella maculipennis) had laid eggs were sprayed until dripping wet. After the treatment the pots were set up in aerated glass cylinders for seven days.

The criterion for evaluation of the action was feed damage on the treated plants in comparison with the feed damage on untreated plants.

|   | COMPOUND | SUBSTANCE CONCENTRATION (%) | FEED DAMAGE IN % |
|---|---|---|---|
| 1. | N-(4-Chlorobenzyl)-N-methyl-2-propinyl amine | 0.05 | 0 |
| 2. | N-Benzyl-N-methyl-2-propinylamine | 0.05 | 0 |

| | COMPOUND | SUBSTANCE CON-CENTRATION (%) | FEED DAMAGE IN % |
|---|---|---|---|
| 3. | 3,4-Dichlorobenzyl-methyl-2-propinyl ammonium chloride | 0.05 | 0 |
| | Comparison Agents | | |
| 4. | trans-2-Phenylcyclopropyl aminosulfate | 0.1 | 100 |
| 5. | 1-Isonicotinyl-2-isopropyl hydrazine phosphate | 0.1 | 100 |

What is claimed herein is:

1. A method for killing insect ova which comprises treatment of a host with ovicidal amount of compound of the general formula

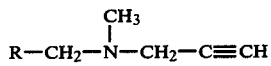

wherein R is an aromatic hydrocarbon radical and acid addition salts of said compounds.

2. The method of claim 1 wherein R is a phenyl radical.

3. The method of claim 2 wherein R is a phenyl radical having from one to three substituents, individually selcted from the group consisting of alkyl groups, having from 1 to 3 carbons; alkoxy groups having from 1 to 3 carbons; chloro; and nitro.

4. The method of claim 2 wherein R is selected from the group consisting of 4-chlorobenzyl; benzyl; 2-chlorobenzyl; 3-chlorobenzyl; 3,4-dichlorobenzyl; 1,3-methoxybenzyl, and the acid addition salts of said compounds.

5. The method according to claim 2 for protecting crop plants against infestation of Egyptian cotton moth, cabbage moth, and cabbage butterfly by killing the ova thereof by treatment of the crop plants with an ovicidal amount of said compound.

6. A method as defined in claim 2 for protecting crop plants of the class consisting of cotton, tomato, cauliflower, bush bean, string bean, sugar beet, corn, rice from infestation by pests of the class consisting of Egyptian cotton moth, cabbage moth, and cabbage butterfly.

7. A method as defined in claim 6 wherein said crop plants are treated with a composition comprising from about 0.1 to 1 percent of a compound selected from the group consisting of:
N-benzyl-N-methyl-2-propinylamine; N-(4-chlorobenzyl)-N-methyl-2-propinylamine; N-(2-chlorobenzyl)-N-methyl-2-propinylamine; N-(3-chlorobenzyl)-N-methyl-2-propinylamine; N-(3,4-dichlorobenzyl)-N-methyl-2-propinylamine; N-(3-methoxybenzyl)-N-methyl-2-propinylamine and acid addition salts thereof.

8. An ovicidal composition for the method of claim 1 which comprises from about 0.01 to about 1.0 percent of a compound selected from the group consisting of N-benzyl-N-methyl-2-propinylamine; N-(4-chlorobenzyl)-N-methyl-2-propinylamine; N-(2-chlorobenzyl)-N-methyl-2-propinylamine; N-(3-chlorobenzyl)-N-methyl-2-propinylamine; N-(2,4-dichlorobenzyl)-N-methyl-2-propinylamine; N-(3,4-dichlorobenzyl)-N-methyl-2-propinylamine; N-(3-methoxybenzyl)-N-methyl-2-propinylamine and acid addition salts thereof.

* * * * *